US00PP30151P2

(12) United States Plant Patent
Horvath

(10) Patent No.: US PP30,151 P2
(45) Date of Patent: Jan. 29, 2019

(54) ***ALLIUM* HYBRID PLANT NAMED 'CHIVETTE'**

(50) Latin Name: ***Allium* hybrid**
Varietal Denomination: Chivette

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 15/530,218

(22) Filed: Dec. 14, 2016

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

A new, distinct *Allium* hybrid plant as shown and described, characterized by thin arching green foliage in combination with light purple flowers, on mostly sterile plants.

1 Drawing Sheet

Figure 1:
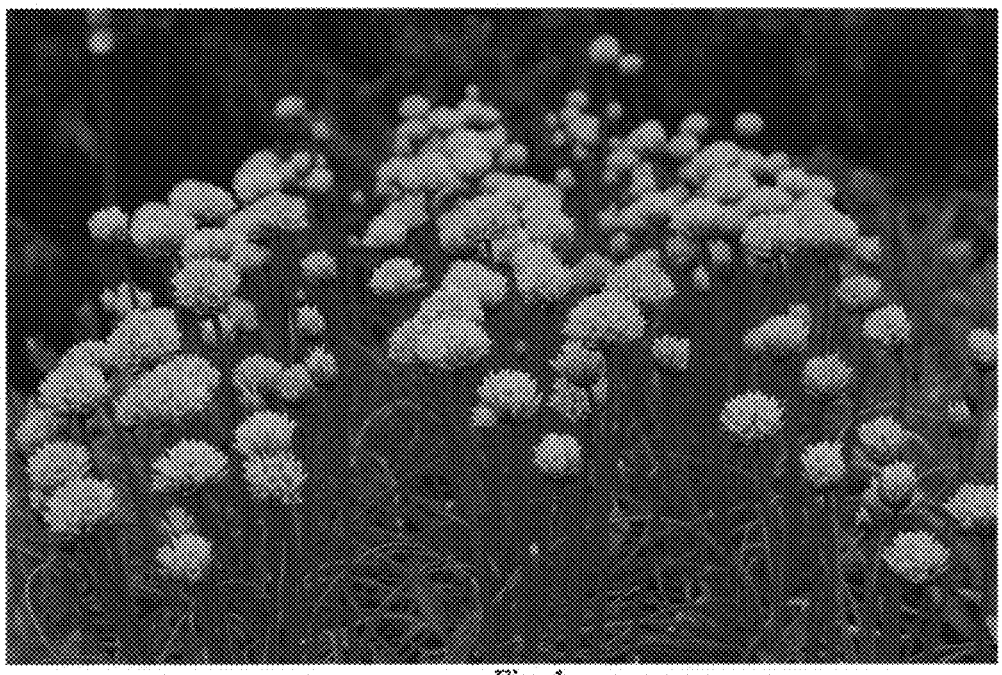

Latin name: *Allium* hybrid.
Cultivar name: 'Chivette'.

BACKGROUND OF THE INVENTION

The present invention relates to a new and distinct hybrid of *Allium* hybrid plant named 'Chivette' characterized by thin green arching foliage, spring blooming plants with light purple flowers, on mostly sterile plants. The new *Allium* hybrid was the result of a breeding program taking place in Hebron, Ill. since 2010. 'Chivette' arose as a selection from seed sown from open pollination of unnamed plants of *Allium*. The exact parentage of *Allium* hybrid 'Chivette' is unknown, however the female or seed parent is believed to be an unnamed *Allium schoenoprasum*, while the male pollen parent is unknown. The selection of the new plant was due to its' thin arching green foliage in combination with light purple flowers, on mostly sterile plants. Asexual propagation by division has been the means of reproduction. The initial division propagation has taken place at a nursery in Hebron, Ill. in 2015. The new *Allium* hybrid has shown to be stable and identical in reproduction to the parent after dividing over 250 plants from 2015 to 2016.

SUMMARY OF THE INVENTION

The new *Allium* hybrid plant named 'Chivette' characterized by thin green arching foliage in combination with light purple flowers on mostly sterile plants, have been observed to be unique and stable.

Plants of the new *Allium* hybrid plant named 'Chivette' can be compared to the likely female or seed parent, *Allium schoenoprasum*, not patented. 1. The new plant height is typically 33 cm tall while *Allium schoenoprasum* is typically 45 cm tall. 2. The new plant also has wider green foliage RHS color 146 A measuring 5-6 mm wide, while *Allium schoenoprasum*, has greyed green foliage, RHS color not recorded, measuring 3 mm wide. 3. *Allium* hybrid 'Chivette' is mostly sterile, white *Allium schoenoprasum* is fertile and produces many seeds per flower.

Plants of the new *Allium* hybrid can also be compared to plants of *Allium* hybrid 'Millenium', not patented. 1. The new plant height is typically 33 cm tall while *Allium* hybrid 'Millenium' is typically 50 cm tall. 2. The new plant also has thinner green foliage measuring 6 mm while *Allium* hybrid 'Millenium', has wider green foliage measuring 15 mm wide. 3. The new plant has lighter colored flower 85 A compared *Allium* hybrid 'Millenium' dark purple flowers, RHS color not measured.

DESCRIPTION OF PHOTOGRAPHS

FIG. 1. A blooming plant in May on a 2 year old plant in Hebron, Ill. USA.

Figure 2:
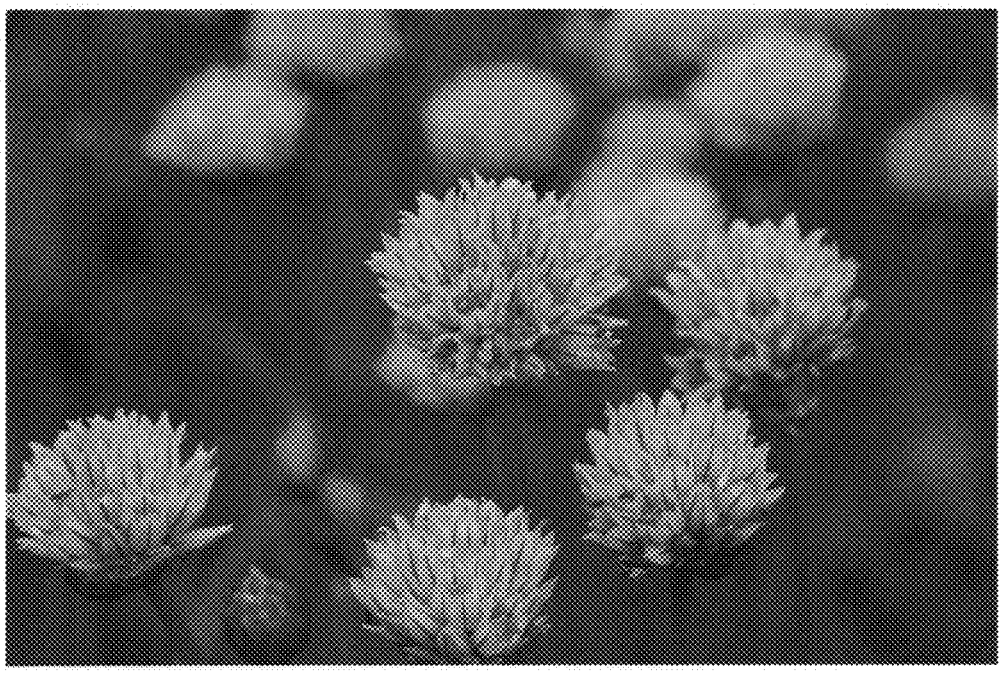

FIG. 2. A close up of the flowers in May on a 2 year old plant in Hebron, Ill. USA.

DETAILED BOTANICAL DESCRIPTION

In the following description, color references are made to The Royal Horticultural Society Colour Chart (2001). Plants used for the description were grown in a one gallon container for two years at a nursery in Hebron, Ill. Measurements and numerical values represent averages of typical plants.

Botanical classification: *Allium* hybrid cultivar 'Chivette'.
Parentage: Unknown.
Propagation: Vegetative division.
Plant description:

*Type*.—Herbaceous perennial. The overall habit of the new *Allium* hybrid is a basal tuft of green linear foliage arising from bulbous roots, with terminal light purple flower clusters in May, on mostly sterile plants.

*Hardiness*.—USDA zones 3-9.
*Plant height*.—33 cm.
*Plant width*.—50 cm.

Stem description:

*Stem shape*.—Round with ridges, hallow.
*Stem size*.—Diameter — 3 mm.
*Stem length*.—30 cm.
*Internodes*.—None.
*Stem coloration*.—Stem color 144 A.
*Stem texture*.—Smooth, and glabrous.

*Roots*.—Fibrous below the bulb, color 158 A.

*Bulb*.—Size — 12 mm wide at the base, 7 mm wide at the top where the foliage begins, 25 mm in length, color: ranges from 158 B.

Foliage description:

*Shape*.—Linear.

*Arrangement*.—Basal, alternate.

*Leaf blade size*.—Length: up to 53 cm, Width: 6 mm.

*Margins*.—Entire.

*Petiole*.—None.

*Leaf apex*.—Acute.

*Leaf base*.—Attenuate.

*Leaf quantity*.—An average of 4 per stem.

*Texture*.—Upper and lower surfaces: smooth, glabrous.

*Adaxial and abaxial leaf color description*.—146 A.

*Venation pattern*.—Parallel.

*Venation color*.—Upper 146 A, lower 146 A.

Flower description:

*Inflorescence type*.—Umbel, round, held on a leafless stalk.

*Umbel size*.—Length: 22 mm tall, width: 28 mm.

*Peduncle size and color*.—Length: 30 cm, diameter: 3 mm, color — 144 A.

*Peduncle texture*.—Smooth, glabrous.

*Pedicel size and color*.—Length: 1-2 mm, diameter: 1 mm, color — 144 A.

*Flower bud*.—Size: length: 22 mm, diameter: 22 mm.

*Flower bud surface*.—Smooth, glabrous.

*Flower bud shape*.—Ovoid, tubular, constricted at the base.

*Flower bud color*.—N 74 C.

*Corolla description*.—5 petals unfused, constricted at the base.

*Petal apex*.—Entire, acute.

*Petal base*.—Unfused.

*Petal margin*.—Entire.

*Petal texture*.—Outer surface: smooth, inside surface: smooth.

*Petal color*.—Outer surface — is color 85 A, inside surface — color is 85 A.

*Calyx shape*.—Stellate.

*Calyx size*.—Length: 9 mm, Width: 4 mm.

*Calyx color*.—85 A with 83 A stripe down the middle.

*Sepal quantity and arrangement*.—3, unfused.

*Sepal size*.—Length: 9 mm, diameter: 4 mm at base coming to a point.

*Sepal shape*.—Lanceolate, apex: acute, base: cuneate, margin: entire.

*Sepal texture*.—Upper and lower surfaces: smooth, glabrous.

*Sepal color*.—Adaxial color 85 A, Abaxial color 85 A with purple stripe 83 A down the center.

*Flower type and shape*.—Bowl, comprised of 3 sepals and 3 petals.

*Flower color*.—85 A outside, 85 A inside.

*Flower size*.—Length: 9 mm, width: 4 mm.

*Flower number*.—45 per umbel, 900 per plant with up to 20 flowering stems.

*Bloom period and duration*.—3 weeks the beginning of May in Hebron, Ill.

*Flower longevity and duration on the plant*.—Approximately 3 weeks.

*Flower longevity and duration cut*.—Not measured.

*Scent*.—None.

Reproductive organs:

*Stamen*.—Quantity: 6, length: 3 mm, diameter: less than 1 mm at the base getting thinner toward the tip.

*Anther*.—Quantity: 6, length: 1 mm, diameter: less than 1 mm.

*Anther shape*.—Linear, color not measured.

*Filament*.—155 A.

*Pollen*.—Sparse, color: RHS 155 A.

*Pistil*.—Number: 1, length: 2 mm, width: less than 1 mm, color — 155 A.

*Stigma shape*.—Conical, color — 155 A.

*Style*.—Number: 1, length: 1-2 mm, width less than 1 mm.

*Ovaries*.—Made of 3 carpels, length: 2 mm, width: 2 mm.

*Fruit*.—Capsule more or less round, 2-3 mm long, 2-3 mm wide, glabrous, color 202 A. Very few per flower, 5 at the most. The seed has not been determined as viable seed.

Disease resistance: Resistance to diseases common to *Allium* has not been observed on plants grown under nursery conditions.

I claim:

1. A new, distinct *Allium* hybrid plant as shown and described, characterized by thin arching green foliage in combination with light purple flowers, on mostly sterile plants.

* * * * *